(12) United States Patent
Yamaguchi et al.

(10) Patent No.: US 8,080,434 B2
(45) Date of Patent: Dec. 20, 2011

(54) NONDESTRUCTIVE TESTING METHOD FOR OXIDE SEMICONDUCTOR LAYER AND METHOD FOR MAKING OXIDE SEMICONDUCTOR LAYER

(75) Inventors: Norihiko Yamaguchi, Kangawa (JP); Satoshi Taniguchi, Kangawa (JP); Masao Ikeda, Kanagawa (JP)

(73) Assignee: Sony Corporation, Tokyo (JP)

( * ) Notice: Subject to any disclaimer, the term of this patent is extended or adjusted under 35 U.S.C. 154(b) by 99 days.

(21) Appl. No.: 12/622,095

(22) Filed: Nov. 19, 2009

(65) Prior Publication Data
US 2010/0129942 A1 May 27, 2010

(30) Foreign Application Priority Data
Nov. 21, 2008 (JP) .................. 2008-298292

(51) Int. Cl.
H01L 21/66 (2006.01)

(52) U.S. Cl. .................. 438/16; 438/1; 438/7; 438/44; 438/46; 438/69; 257/E21.53

(58) Field of Classification Search .................. None
See application file for complete search history.

(56) References Cited

U.S. PATENT DOCUMENTS
2004/0253759 A1* 12/2004 Garber et al. .................. 438/46

FOREIGN PATENT DOCUMENTS
JP 2000-28518 1/2000
JP 2006-165529 6/2006

OTHER PUBLICATIONS

Mikio Yamazaki et al, Photo luminescence of a polycrystalline ZnO sputter film, 47th Applied physics-related association proceedings, Japan, Society of Applied Physics, Mar. 2000, p. 579.
Japanese Office Action issued Dec. 14, 2010, for corresponding Japanese Appln. No. 2008-298292.

* cited by examiner

*Primary Examiner* — N Drew Richards
*Assistant Examiner* — Kyoung Lee
(74) *Attorney, Agent, or Firm* — K&L Gates LLP

(57) ABSTRACT

A nondestructive testing method for an oxide semiconductor layer includes the steps of applying excitation light to an amorphous or polycrystalline target oxide semiconductor layer to be tested and measuring an intensity of photoluminescence in a wavelength region longer than a wavelength corresponding to a bandgap energy among light emitted from the target oxide semiconductor layer; and estimating a film property of the target oxide semiconductor layer on the basis of measurement results.

13 Claims, 6 Drawing Sheets

NONDESTRUCTIVE TESTING METHOD FOR OXIDE SEMICONDUCTOR LAYER AND METHOD FOR MAKING OXIDE SEMICONDUCTOR LAYER

CROSS REFERENCES TO RELATED APPLICATIONS

The present application claims priority to Japanese Priority Patent Application JP 2008-298292 filed in the Japan Patent Office on Nov. 21, 2008, the entire content of which is hereby incorporated by reference.

BACKGROUND

The present application relates to a testing method for investigating in a noncontact and nondestructive manner the film property of an amorphous or polycrystalline oxide semiconductor layer useful as an active layer of a thin film transistor or the like, and to a method for making an amorphous or polycrystalline oxide semiconductor layer utilizing the testing method.

Field effect transistors (FETs) designed as thin film transistors (TFTs) are widely used as pixel transistors in electronic circuits, in particular, active matrix circuits of image display devices. Currently available TFTs generally use amorphous silicon or polycrystalline silicon as a semiconductor material constituting active layers, and glass substrates as substrates.

However, glass substrates are heavy, readily break upon impact, and have no flexibility. Thus, research and development on light-weight, flexible plastic substrates that are not easily breakable and can replace glass substrates is now under way. Since a high-temperature heat treatment process is required for making silicon thin films, it is difficult to form silicon thin films on plastic substrates having low heat resistance. This has led to a focus on amorphous or polycrystalline metal oxide semiconductor materials that can be formed into films at low temperature and serve as a semiconductor material that replaces silicon.

For example, Japanese Unexamined Patent Application Publication No. 2006-165529 ('529 document) (pp. 6 to 9, 16, 21, and 222, and FIG. 3) proposes an amorphous oxide based on In—Ga—Zn—O or the like containing indium, gallium, and zinc as main constituent elements. This amorphous oxide is characterized in that it includes crystallites, has a composition that varies in the layer thickness direction, or contains at least one predetermined element, and in that it has an electron carrier density less than $10^{18}/cm^3$ or shows a tendency that the electron mobility increases with the electron carrier density. This document provides the following description.

When an amorphous oxide represented by a compositional formula, $Zn_xGa_yIn_zO_{x+3y/2+3z/2}$ or the like is formed into films by regular sputtering techniques, oxygen defects are readily formed and a large number of carrier electrons are generated, thereby giving an electron carrier density of $10^{18}/cm^3$ or more and an electrical conductivity of 10 S/cm or more. This oxide is a useful conductor but is rarely used to make normally off TFTs because when this oxide is used in active layers of TFTs, a large electrical current flows between the source electrode and the drain electrode in the absence of a gate voltage. Moreover, it is also difficult to increase the ON/OFF ratio.

However, in the case where an In—Ga—Zn—O-based amorphous oxide is formed into films by vapor deposition techniques such as pulsed laser deposition or sputtering using a target composed of a polycrystalline sinter represented by a compositional formula, $InGaO_3(ZnO)_m$ (m is a natural number less than 6), the number of oxygen defects can be reduced by maintaining the oxygen partial pressure in the deposition atmosphere to a particular level or higher, and as a result, the electron carrier density can be suppressed to less than $10^{18}/cm^3$. The electron mobility observed was more than 1 $cm^2/$(V·sec), leading to the finding of a unique characteristic that the electron mobility increases with the number of conduction electrons. A flexible TFT that has desired properties and is transparent under visible light can be made if its active layer can be formed by using this amorphous oxide.

The amount of oxygen deficiency in the amorphous oxide can also be controlled by processing the oxide film in an oxygen-containing atmosphere after the deposition. During this process, in order to effectively control the amount of oxygen deficiency, the temperature of the oxygen-containing atmosphere is controlled to preferably 0° C. to 300° C., more preferably 25° C. to 250° C., and most preferably 100° C. to 200° C.

FIG. 6 is a graph disclosed in the '529 document showing the relationship between the oxygen partial pressure in the atmosphere and the electrical conductivity of the oxide semiconductor layer in the case where an In—Ga—Zn—O amorphous oxide semiconductor layer is formed by sputtering. FIG. 6 shows that assuming that the adequate electrical conductivity is $10^{-6}$ to 10 S/cm, the oxygen partial pressure is desirably controlled within a narrow range of $3 \times 10^{-2}$ to $5 \times 10^{-2}$ Pa.

When the oxide semiconductor layer is used as an active layer of a FET, the carrier density in the oxide semiconductor layer is a parameter crucial for determining the element characteristics. However, as shown in FIG. 6, the carrier density in the oxide semiconductor layer is highly sensitive to the deposition conditions. Moreover, since the carrier density in the oxide semiconductor layer is unstable, it changes by a magnitude of several orders depending on the atmosphere and the temperature of the steps and chemical treatment subsequent to the deposition process. Thus, the carrier density is adjusted by an annealing process under a controlled atmosphere.

If the carrier density of the oxide semiconductor layer during deposition, during annealing, or upon completion of fabrication can be quickly checked by nondestructive testing, oxide semiconductor layers and eventually semiconductor elements such as FETs can be fabricated in a high production yield.

In general, the carrier density of a semiconductor layer is determined by measurement that utilizes the Hall effect. However, the Hall effect measurement is not suitable for quickly determining the carrier density nondestructively since a Hall element for the Hall effect measurement is prepared.

On the other hand, Japanese Unexamined Patent Application Publication No. 2000-28518 ('518 document) (pp. 2-4 and FIG. 1) reports an example of measuring the carrier density by a photoluminescence technique. FIG. 7 is a spectrum of the photoluminescence from the InGaAs epitaxial film disclosed in the '518 document. FIG. 7 shows that the spectrum of the photoluminescence emitted from single crystals has a peak at a wavelength corresponding to the bandgap energy. The carrier density can be derived by analyzing the shape of the peak. However, photoluminescence is rarely observed from amorphous or polycrystalline oxide semiconductor layers at a wavelength corresponding to the bandgap energy. Thus, the technique disclosed in the '518 document is not applicable.

SUMMARY

It is desirable to provide a testing method that can quickly and nondestructively investigate the film property of an amorphous or polycrystalline oxide semiconductor layer useful as an active layer for a TFT or the like, and a method for making an amorphous or polycrystalline oxide semiconductor layer using the testing method.

One embodiment of the present application provides a nondestructive testing method for an oxide semiconductor layer. The method includes steps of applying excitation light to an amorphous or polycrystalline target oxide semiconductor layer to be tested and measuring an intensity of photoluminescence in a wavelength region longer than a wavelength corresponding to a bandgap energy among light emitted from the target oxide semiconductor layer, and estimating a film property of the target oxide semiconductor layer on the basis of measurement results.

Another embodiment provides a method for making an oxide semiconductor layer. The method includes steps of depositing an amorphous or polycrystalline oxide semiconductor layer on a substrate, and testing a film property of the amorphous or polycrystalline oxide semiconductor layer by the nondestructive testing method described above.

The nondestructive testing method for the oxide semiconductor layer described above can be performed easily and quickly because the method involves applying excitation light to the amorphous or polycrystalline target oxide semiconductor layer to be tested to measure the intensity of photoluminescence emitted from the target oxide semiconductor layer. Moreover, as described in First Embodiment below, the intensity measured by the nondestructive testing method, i.e., the intensity of the photoluminescence in the wavelength region longer than the wavelength corresponding to the bandgap, is closely linked with the film property of the target oxide semiconductor layer. Thus, the film property of the target oxide semiconductor layer can be reliably estimated nondestructively and noncontactingly.

According to the above-described method for making the oxide semiconductor layer, amorphous or polycrystalline oxide semiconductor layers can be fabricated with good control accuracy, at high productivity, and in high production yield since the method includes the step of testing the film property of the amorphous or polycrystalline oxide semiconductor layer by using the nondestructive testing method for the oxide semiconductor layer described above.

The nondestructive testing method described above may further include a step of measuring a photoluminescence intensity of an amorphous or polycrystalline reference oxide semiconductor layer in the same manner as that of the target oxide semiconductor layer and measuring a film property of the reference oxide semiconductor layer so as to obtain a relationship between the photoluminescence intensity and the film property, the reference oxide semiconductor layer having the same element composition as and being prepared by the same process and at the same deposition temperature as the target oxide semiconductor layer. Then, the film property of the target oxide semiconductor layer may be estimated on the basis of this relationship.

In such a case, the film property of the reference oxide semiconductor layer measured is preferably a carrier density and a carrier density of the target oxide semiconductor layer is preferably estimated on the basis of a relationship between the photoluminescence intensity and the carrier density of the reference oxide semiconductor layer. The carrier density of the reference oxide semiconductor layer can be measured by using a Hall effect.

The nondestructive testing method can noncontactingly test an oxide semiconductor layer serving as an active layer incorporated in a semiconductor element.

In the method for making an oxide semiconductor layer described above, the film property of the amorphous or polycrystalline oxide semiconductor layer during deposition is preferably monitored in situ by the nondestructive testing method and a deposition condition is preferably controlled on the basis of monitored results so that a desired film property is obtained. More preferably, at least one deposition condition selected from an oxygen partial pressure in a deposition atmosphere, a substrate temperature, and a deposition rate is controlled.

The method for making an oxide semiconductor layer preferably further includes a step of annealing the amorphous or polycrystalline oxide semiconductor layer. Preferably, the film property of the amorphous or polycrystalline oxide semiconductor layer is tested by the nondestructive testing method after deposition, the annealing is performed after the testing, and an annealing condition is set on the basis of results of the nondestructive testing so that a desired film property is obtained.

Alternatively, the method preferably further includes a step of annealing the amorphous or polycrystalline oxide semiconductor layer after deposition, in which the film property of the amorphous or polycrystalline oxide semiconductor layer during annealing is monitored in situ by the nondestructive testing method and an annealing condition is controlled on the basis of monitored results so that a desired film property is obtained. In such a case, at least one annealing condition selected from an oxygen partial pressure in an annealing atmosphere, an annealing temperature, and an annealing time is preferably controlled.

The method for making an oxide semiconductor layer is preferably a part of a process for producing a semiconductor element that includes the amorphous or polycrystalline oxide semiconductor layer serving as an active layer and preferably further includes a step of testing the film property of the amorphous or polycrystalline oxide semiconductor layer by the nondestructive testing method after the amorphous or polycrystalline oxide semiconductor layer is made. The step to be taken next is preferably selected on the basis of results of the nondestructive testing.

Additional features and advantages are described herein, and will be apparent from the following Detailed Description and the figures.

DETAILED DESCRIPTION

The present application will be described with reference to the drawings according to an embodiment.

First Embodiment

In a first embodiment, examples of a nondestructive testing method for an oxide semiconductor layer are mainly described.

Figure 1A:
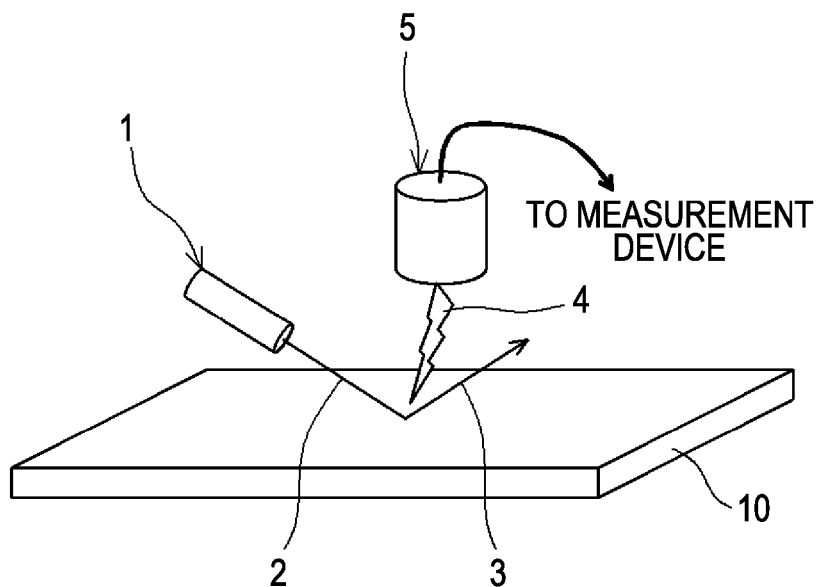
FIG. 1A is a schematic diagram showing a nondestructive testing method for testing a film property of an oxide semiconductor layer according to a first embodiment.

FIG. 1A is a schematic diagram showing a nondestructive testing method for the oxide semiconductor layer according to the first embodiment. According to the system shown in FIG. 1A, excitation light 2 from an excitation light source 1 is applied to an oxide semiconductor layer on a substrate 10 and photoluminescence 4 is detected with a photodetector 5. The excitation light source 1 is preferably a laser light source. The wavelength of the excitation light 2 is desirably shorter than the wavelength corresponding to the bandgap energy of the oxide semiconductor layer.

Figure 1B:
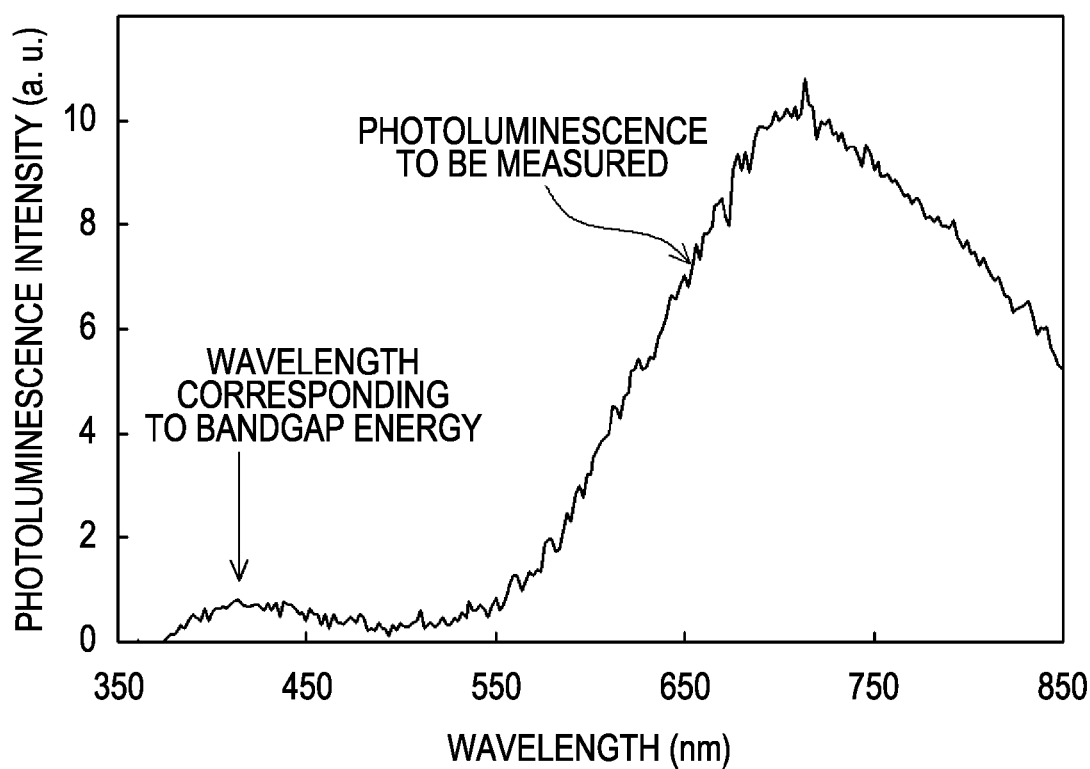
FIG. 1B is a photoluminescence spectrum obtained by the nondestructive testing method.

FIG. 1B is a photoluminescence spectrum obtained by irradiating an In—Ga—Zn—O-based oxide semiconductor layer formed by sputtering with a 325 nm He—Cd laser beam (output: 1 W/cm$^2$) at 77 K. For single crystals, the photoluminescence is most intense near an wavelength of 410 nm corresponding to the bandgap energy. However, for amorphous or polycrystalline oxide semiconductor layers, the photoluminescence at a wavelength corresponding to the bandgap energy is weak. Thus, it is difficult to estimate the carrier density from the photoluminescence spectrum at the wavelength corresponding to the bandgap energy as has been done in the '518 document.

The inventors of the present application have found that, for amorphous or polycrystalline oxide semiconductor layers, intense photoluminescence is detected in the wavelength region longer than the wavelength corresponding to the bandgap energy and that there is a close link between the intensity of the photoluminescence in this wavelength region and the film property of the amorphous or polycrystalline oxide semiconductor layer.

Figure 2:
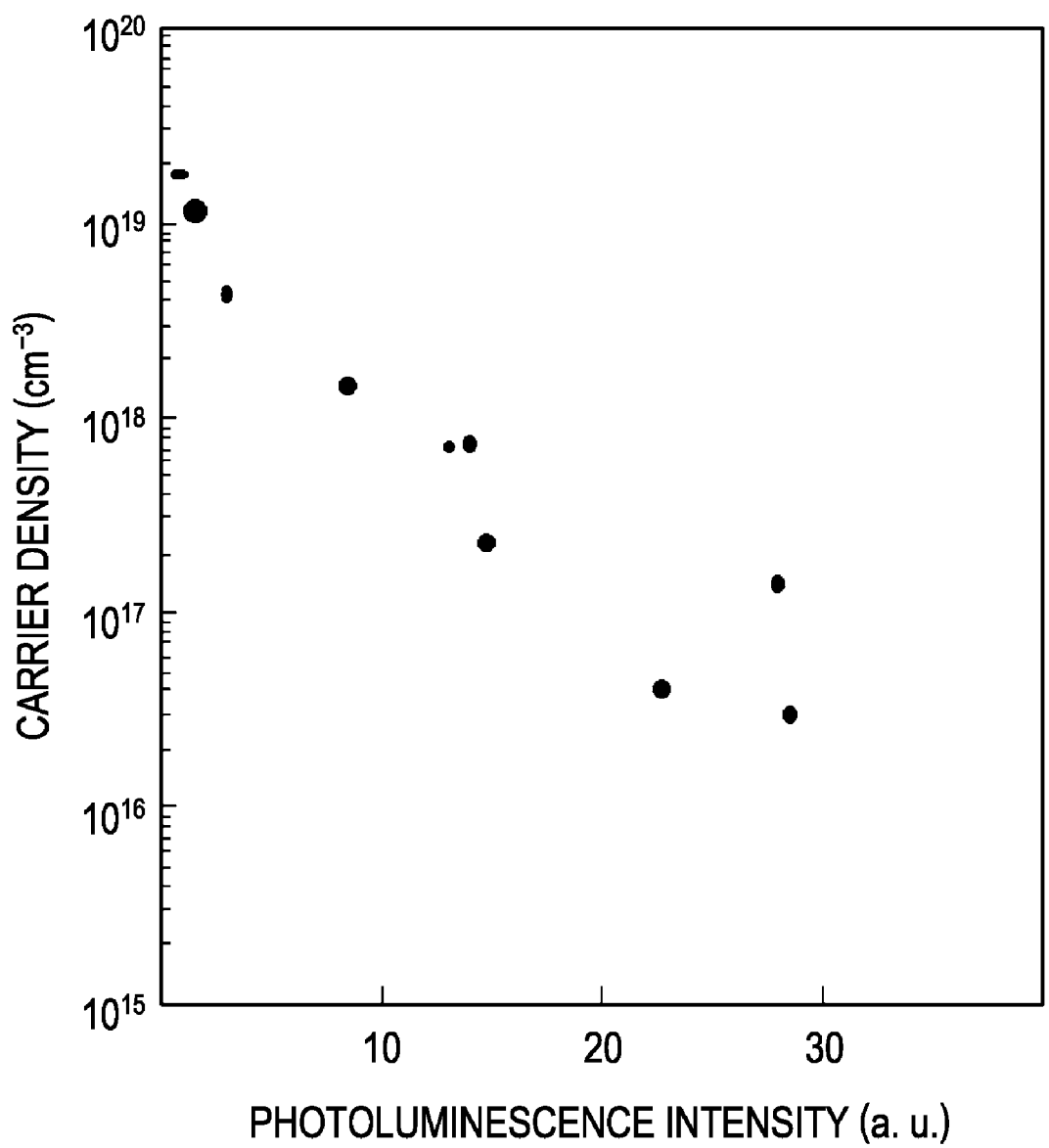
FIG. 2 is a graph showing the relationship between the photoluminescence intensity and the carrier density of a reference oxide semiconductor layer.

FIG. 2 is a graph showing the relationship between the peak intensity of the photoluminescence and the carrier density in the amorphous or polycrystalline oxide semiconductor layer. Note here that the method for making the oxide semiconductor layer is described in Second Embodiment below. Every time the test is conducted, the intensity of the photoluminescence is corrected by using as a reference the intensity of the photoluminescence from a gallium nitride substrate measured by the same optical system. The carrier density of the oxide semiconductor layer is determined by Hall measurement.

FIG. 2 shows that a substantially linear relationship is established between the logarithm of the carrier density and the peak intensity of the photoluminescence. The photoluminescence that appears in the wavelength region longer than the wavelength corresponding to the bandgap energy is thought to be the emission from the defect level such as oxygen defects from the energy viewpoint. Thus, the intensity of the photoluminescence in such a wavelength region is thought to reflect the defect density and thereby have a close link with the carrier density.

Therefore, the film property of the target oxide semiconductor layer can be estimated nondestructively and noncontactingly by measuring the intensity of the photoluminescence in the wavelength region longer than the wavelength corresponding to the bandgap energy among the light emitted from the amorphous or polycrystalline target oxide semiconductor layer irradiated with excitation light.

However, thorough studies conducted by the inventors have revealed that the profile of the photoluminescence spectrum changes depending on the element constitution of the oxide semiconductor layer, the method by which the oxide semiconductor layer is made, and the deposition temperature. Thus, in order to accurately estimate the film property such as carrier density, it is desirable to prepare an amorphous or polycrystalline reference oxide semiconductor layer having the same element composition by the same process and at the same film-forming temperature as the target oxide semiconductor layer and to measure the intensity of the photoluminescence and the film property of this reference oxide semiconductor layer in the same manner as the target oxide semiconductor layer. In this manner, the relationship between the photoluminescence intensity and the film property (e.g., the relationship shown in FIG. 2) can be obtained in advance and the film property of the target oxide semiconductor layer can be estimated on the basis of this relationship. The intensity of the photoluminescence to be measured here may be a peak intensity or an intensity in a wavelength region with an adequate breadth.

According to the nondestructive testing method for the oxide semiconductor layer described above, light is used as a probe to measure the carrier density nondestructively and noncontactingly. Thus, the carrier density of an oxide semiconductor layer serving as an active layer incorporated in a semiconductor element or that of a semiconductor element in operation can be measured by this method.

Second Embodiment

In a second embodiment, examples of a method for making a field effect transistor (FET) that includes an amorphous or polycrystalline oxide semiconductor layer serving as an active layer are mainly described. In this embodiment, an In—Ga—Zn—O oxide layer is formed as an oxide semiconductor layer.

FIGS. 3A to 3D are partial cross-sectional views showing a flow of a process of making a FET 20 constituted as a thin film transistor according to the second embodiment. The process for making the FET 20 will now be described with reference to the drawings.

Figure 3A:
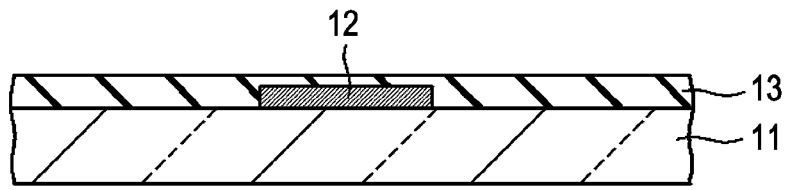
FIGS. 3A to 3D are partial cross-sectional views showing a flow of a process of making a field effect transistor according to a second embodiment.

As shown in FIG. 3A, a gate electrode 12 is formed on an insulating substrate 11. The insulating substrate 11 is not particularly limited. For example, the insulating substrate 11 may be a glass or plastic substrate. The material and method for making the gate electrode 12 are also not particularly limited. For example, molybdenum (Mo) may be used as a gate electrode material and formed into a film by sputtering on the entire surface of the insulating substrate 11, followed by patterning by photolithography or dry-etching. Then a gate insulating film 13 is formed on the entire surface of the insulating substrate 11. The material for the gate insulating film 13 is not particularly limited. For example, a silicon oxide film or a silicon nitride film may be formed.

Figure 3B:
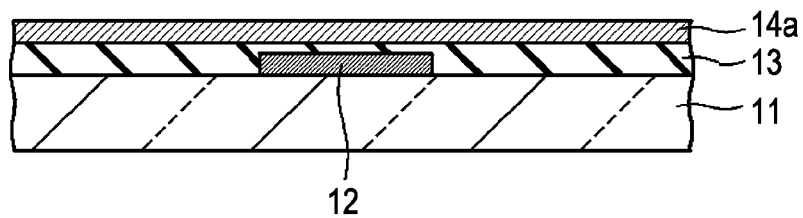
Figure 3C:
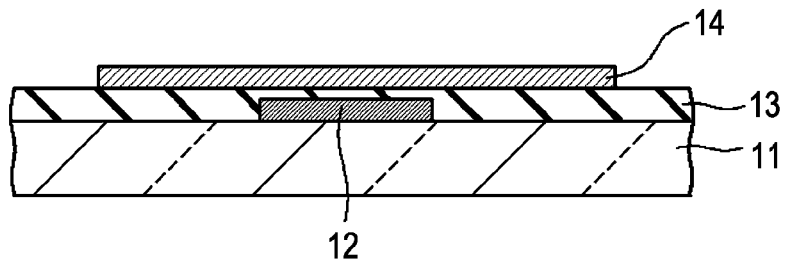

Next, as shown in FIG. 3B, an oxide semiconductor layer 14a that will form an active layer of the FET 20 is formed on the entire surface of the gate insulating film 13 on the insulating substrate 11. The oxide semiconductor layer 14a is formed of an In—Ga—Zn—O-based oxide by sputtering using an InGaZnO$_4$ polycrystalline sinter as a target. Then as shown in FIG. 3C, the oxide semiconductor layer 14a is patterned by etching to form a patterned oxide semiconductor layer 14.

The deposition conditions, composition, and thickness of the oxide semiconductor layer 14a are as follows:

oxygen partial pressure: $1 \times 10^{-2}$ Pa

DC power: 400 W deposition temperature (substrate temperature): room temperature composition: InGaZnO$_4$ thickness: 50 nm Note that the relationship shown in FIG. 2 is obtained from a reference oxide semiconductor layer fabricated under the same conditions as above.

Figure 3D:
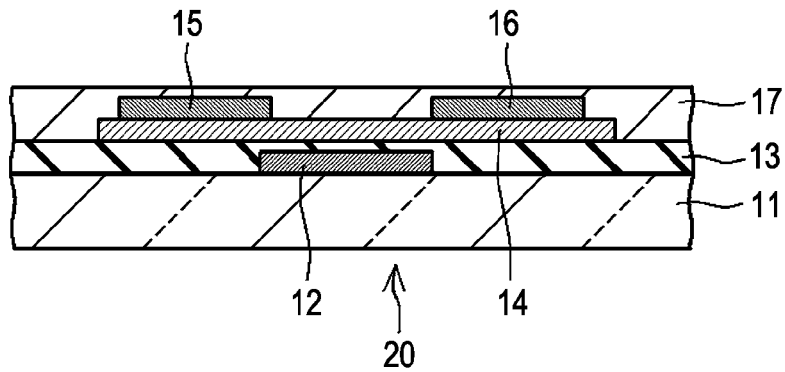

Next, as shown in FIG. 3D, a source electrode 15 and a drain electrode 16 are formed. The material and the method for forming the source electrode 15 and the drain electrode 16 are not particularly limited. For example, molybdenum may be used as a material and the electrodes may be made by patterning molybdenum by photolithography or dry etching. Next, a protective film 17 is formed on the entire surface.

During operation of the FET 20 made as such, a channel region is formed in the oxide semiconductor layer 14 near the gate insulating film 13 and between the source electrode 15 and the drain electrode 16 by the gate voltage applied to the gate electrode 12. The current flowing in the channel region is controlled by the gate voltage.

In various stages of the process for making the FET 20 described above, the nondestructive testing method for the oxide semiconductor layer can be applied. These steps will now be described.

Figure 4:
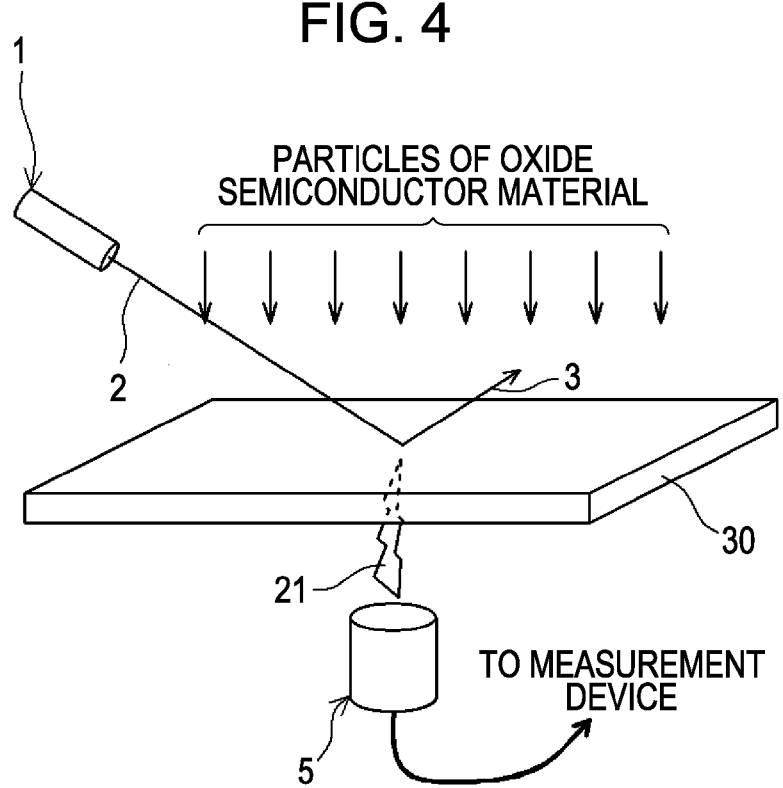
FIG. 4 is a schematic diagram illustrating an example in which a nondestructive testing method for an oxide semiconductor layer is performed in a step of depositing the oxide semiconductor layer.

FIG. 4 is a schematic view illustrating an example of performing a nondestructive testing method for an oxide semiconductor layer in the step of depositing the oxide semiconductor layer shown in FIG. 3B. In this example, photoluminescence 21 is detected by applying excitation light 2 to the oxide semiconductor layer 14a still in the course of deposition. In this manner, the property of the oxide semiconductor layer 14a in the course of deposition can be monitored in situ by the nondestructive testing method and the deposition conditions can be controlled on the basis of the monitored results so that a desired film property can be obtained. As a result, a complicated process of determining conditions can be eliminated and the process can be shortened by omitting checking. The production yield can also be improved.

A laser light source exhibiting good rectilinear propagation may be used so that the excitation light source 1 can be placed outside the deposition chamber. The photodetector 5 that detects the photoluminescence 21 is placed at a side opposite to the substrate surface on which particles of the oxide semiconductor material deposit. According to this arrangement, the nondestructive testing method can be performed on the oxide semiconductor layer 14a without obstructing the process of depositing the oxide semiconductor layer 14a. However, in this case, the insulating substrate 30 is desirably of a type that transmits the photoluminescence 21.

Preferably, at least one deposition condition selected from the oxygen partial pressure in the deposition atmosphere, the temperature of the insulating substrate, and the deposition rate is controlled. Controlling the oxygen partial pressure is particularly important.

Another example of performing the nondestructive testing method for the oxide semiconductor layer described in the first embodiment will now be described. This example concerns a case where a step of annealing the oxide semiconductor layer 14a or 14 is provided after the step of depositing the oxide semiconductor layer 14a shown in FIG. 3B or after the step of patterning the oxide semiconductor layer 14 shown in FIG. 3C. According to this example, the nondestructive testing method is performed on the deposited oxide semiconductor layer 14a or 14 prior to the annealing step. According to this arrangement, annealing conditions can be set on the basis of the results of the nondestructive testing so that desired film property, e.g., a desired carrier density, can be obtained, and the production yield can be improved.

Preferably, at least one annealing condition selected from the oxygen partial pressure in the annealing atmosphere, the annealing temperature, and the annealing time is controlled. Controlling the oxygen partial pressure is particularly important. Other annealing conditions are not particularly limited. For example, annealing may be conducted at 300° C. for 1 hour. The nondestructive test for the oxide semiconductor layer may be performed on the oxide semiconductor layer 14a before patterning or the oxide semiconductor layer 14 after the patterning. However, for the oxide semiconductor layer 14 after the patterning, the area of the oxide semiconductor layer within the beam irradiation range of the excitation light 2 is smaller during measurement. Thus, it is easier to conduct testing on the oxide semiconductor layer 14a before patterning.

Figure 5:
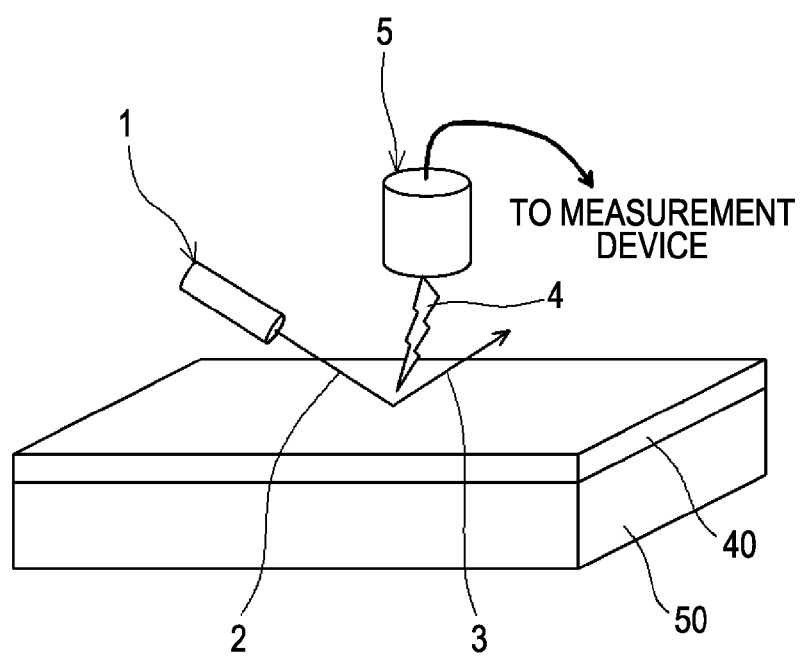
FIG. 5 is a schematic diagram illustrating an example in which a nondestructive testing method for an oxide semiconductor layer is performed in a step of annealing the oxide semiconductor layer.
Figure 6:
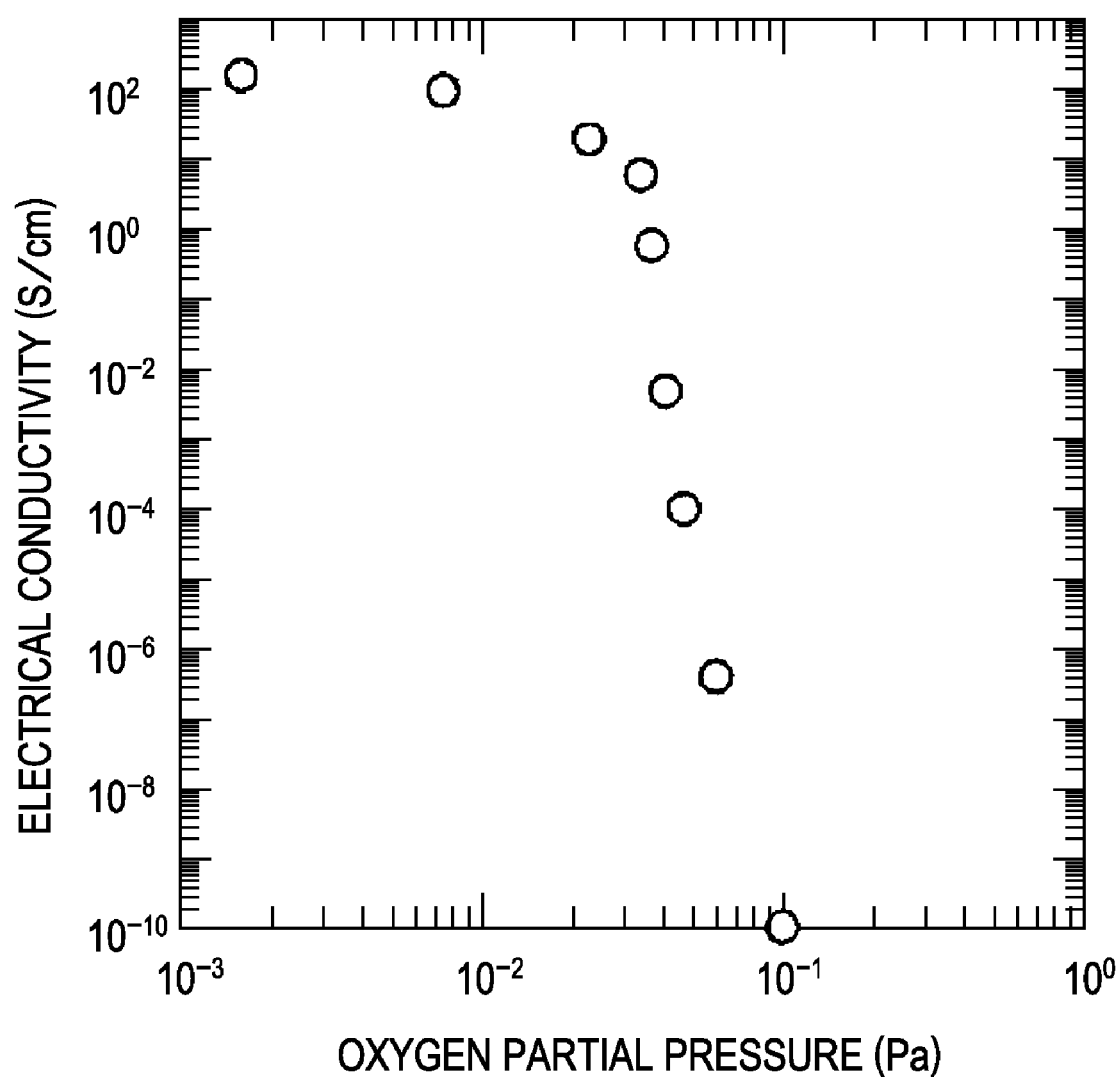
FIG. 6 is a graph disclosed in Japanese Unexamined Patent Application Publication No. 2006-165529 showing the relationship between the oxygen partial pressure in the atmosphere during deposition and the electrical conductivity of an oxide semiconductor layer.
Figure 7:
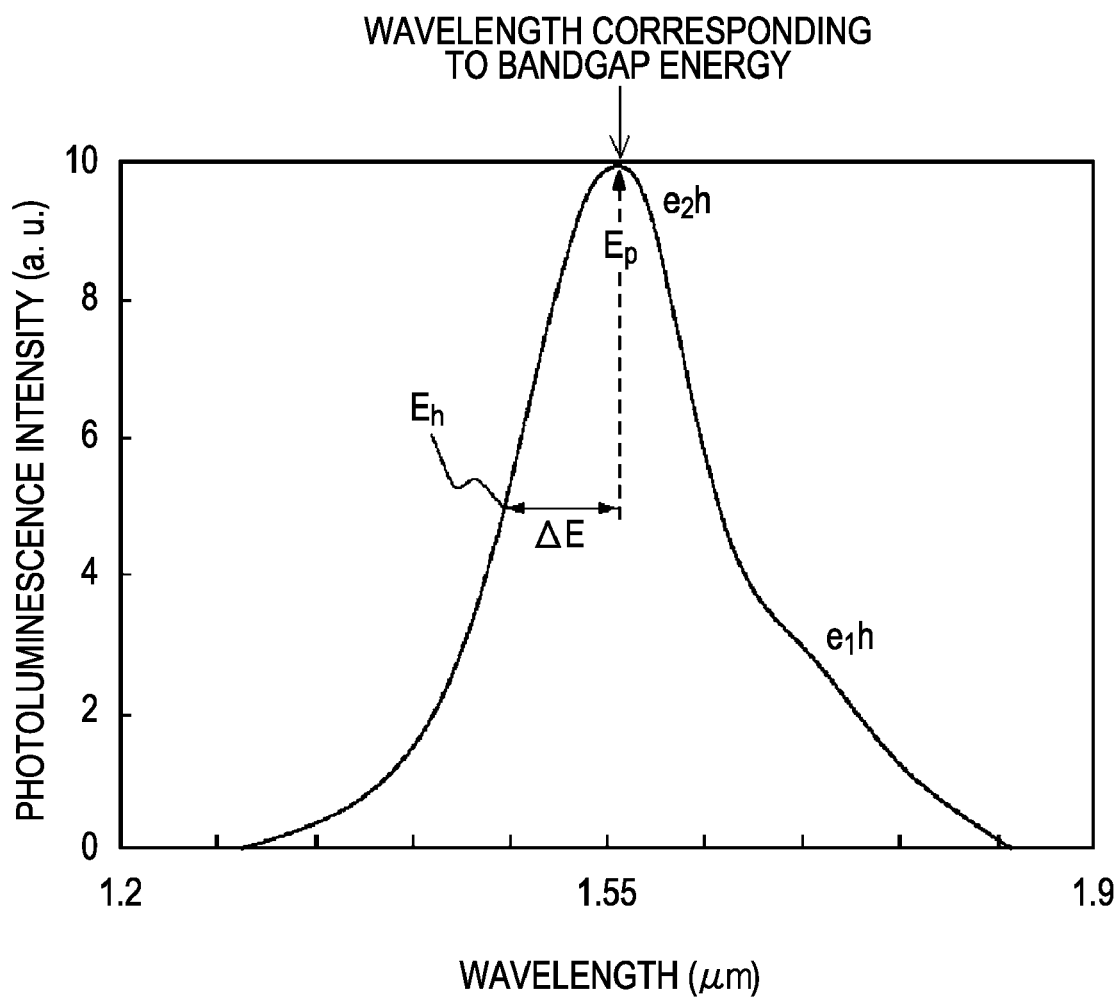
FIG. 7 is a spectrum of photoluminescence from an InGaAs epitaxial film disclosed in the Japanese Unexamined Patent Application Publication No. 2000-28518.

Yet another example of performing the nondestructive testing method for the oxide semiconductor layer involves the case in which the step of annealing the oxide semiconductor layer 14a or 14 is provided as above and the nondestructive testing is performed in the annealing step. FIG. 5 is a schematic diagram illustrating the example in which the nondestructive testing method for the oxide semiconductor layer is performed in the annealing step. In this example, photoluminescence 4 is detected by applying excitation light 2 to the oxide semiconductor layer 14a or 14 during annealing. In this manner, the property of the oxide semiconductor layer in the course of annealing can be monitored in situ by the nondestructive testing method and the annealing conditions can be controlled on the basis of the monitored results so that a desired film property, e.g., carrier density, can be obtained. As a result, a complicated process of determining conditions can be eliminated and the process can be shortened by omitting checking. The production yield can also be improved.

As in the example described above, at least one annealing condition selected from the oxygen partial pressure in the annealing atmosphere, the annealing temperature, and the annealing time is preferably controlled. Controlling the oxygen partial pressure is particularly important. Other annealing conditions are not particularly limited. For example, annealing may be conducted at 300° C. for 1 hour. In FIG. 5, a heater 50 is a device for setting the annealing temperature to a desired temperature. As mentioned earlier, it is easier to conduct the nondestructive test for the oxide semiconductor layer on the oxide semiconductor layer 14a before patterning. Thus, the annealing process under in-situ observation is also easier if conducted on the oxide semiconductor layer 14a before patterning.

The nondestructive testing method for the oxide semiconductor layer can be performed after all steps of making the oxide semiconductor layer 14, e.g., the deposition step, the patterning step, and the annealing step, are completed. In general, the oxide semiconductor layer 14 functions as an active layer incorporated in a semiconductor element, and thus steps for forming the source electrode 15 and the drain electrode 16, the protective film 17, and the semiconductor device are performed after completion of the process of making the oxide semiconductor layer 14 to make a semiconductor element. Thus, it is preferable to conduct nondestructive testing on the oxide semiconductor layer 14 after the process of making the oxide semiconductor layer 14 is finished to check if the resultant product is a pass or fail. In this manner, oxide semiconductor layers 14 that have failed the test will not be processed further and the efficiency can be improved.

The present application contains subject matter related to that disclosed in Japanese Priority Patent Application JP 2008-298292 filed in the Japan Patent Office on Nov. 21, 2008, the entire content of which is hereby incorporated by reference.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A nondestructive testing method for an oxide semiconductor layer, comprising:
  applying excitation light to an amorphous or polycrystalline target oxide semiconductor layer to be tested and measuring an intensity of photoluminescence in a wavelength region longer than a wavelength corresponding to a bandgap energy among light emitted from the target oxide semiconductor layer; and
  estimating a film property of the target oxide semiconductor layer on the basis of measurement results.

2. The nondestructive testing method according to claim 1, further comprising:
  measuring a photoluminescence intensity of an amorphous or polycrystalline reference oxide semiconductor layer in the same manner as that of the target oxide semiconductor layer and measuring a film property of the reference oxide semiconductor layer so as to obtain a relationship between the photoluminescence intensity and the film property, the reference oxide semiconductor layer having the same element composition as and being prepared by the same process and at the same deposition temperature as the target oxide semiconductor layer,
  wherein the film property of the target oxide semiconductor layer is estimated on the basis of this relationship.

3. The nondestructive testing method according to claim 2, wherein the film property of the reference oxide semiconductor layer measured is a carrier density and a carrier density of the target oxide semiconductor layer is estimated on the basis of a relationship between the photoluminescence intensity and the carrier density of the reference oxide semiconductor layer.

4. The nondestructive testing method according to claim 3, wherein the carrier density of the reference oxide semiconductor layer is measured by using a Hall effect.

5. The nondestructive testing method according to claim 1, wherein an oxide semiconductor layer serving as an active layer incorporated in a semiconductor element can be used as the target oxide semiconductor layer and tested noncontactingly.

6. A method for making an oxide semiconductor layer, comprising:
  depositing an amorphous or polycrystalline oxide semiconductor layer on a substrate; and
  testing a film property of the amorphous or polycrystalline oxide semiconductor layer by a nondestructive testing method for an oxide semiconductor layer, comprising:
  applying excitation light to an amorphous or polycrystalline target oxide semiconductor layer to be tested and measuring an intensity of photoluminescence in a wavelength region longer than a wavelength corresponding to a bandgap energy among light emitted from the target oxide semiconductor layer; and
  estimating a film property of the target oxide semiconductor layer on the basis of measurement results.

7. The method according to claim 6, wherein the film property of the amorphous or polycrystalline oxide semiconductor layer during deposition is monitored in situ by the nondestructive testing method and a deposition condition is controlled on the basis of monitored results so that a desired film property is obtained.

8. The method according to claim 7, wherein at least one deposition condition selected from an oxygen partial pressure in a deposition atmosphere, a substrate temperature, and a deposition rate is controlled.

9. The method according to claim 6, further comprising a step of:
  annealing the amorphous or polycrystalline oxide semiconductor layer,
  wherein the film property of the amorphous or polycrystalline oxide semiconductor layer is tested by the nondestructive testing method after deposition,
  the annealing is performed after the testing, and
  an annealing condition is set on the basis of results of the nondestructive testing so that a desired film property is obtained.

10. The method according to claim 6, further comprising:
  annealing the amorphous or polycrystalline oxide semiconductor layer after deposition,
  wherein the film property of the amorphous or polycrystalline oxide semiconductor layer during annealing is monitored in situ by the nondestructive testing method and an annealing condition is controlled on the basis of monitored results so that a desired film property is obtained.

11. The method according to claim 9, wherein at least one annealing condition selected from an oxygen partial pressure in an annealing atmosphere, an annealing temperature, and an annealing time is controlled.

12. The method according to claim 6, wherein the method is a part of a process for producing a semiconductor element that includes the amorphous or polycrystalline oxide semiconductor layer serving as an active layer,
  the method further comprises a step of testing the film property of the amorphous or polycrystalline oxide semiconductor layer by the nondestructive testing method after the amorphous or polycrystalline oxide semiconductor layer is made, and
  a step to be taken next is selected on the basis of results of the nondestructive testing.

13. The method according to claim 12, wherein the semiconductor element is a field effect transistor.

* * * * *